(12) United States Patent
Invernizzi

(10) Patent No.: US 10,664,699 B2
(45) Date of Patent: May 26, 2020

(54) DEVICE AND METHOD OF CALIBRATION FOR AN EYE TRACKER AND EYE CONTROL EQUIPMENT COMPRISING SAID CALIBRATION DEVICE

(71) Applicant: SR LABS S.R.L., Brescia (IT)

(72) Inventor: Paolo Invernizzi, Milan (IT)

(73) Assignee: SR LABS S.R.L., Brescia (IT)

( * ) Notice: Subject to any disclaimer, the term of this patent is extended or adjusted under 35 U.S.C. 154(b) by 556 days.

(21) Appl. No.: 15/317,061

(22) PCT Filed: Jun. 12, 2015

(86) PCT No.: PCT/IB2015/054478
§ 371 (c)(1),
(2) Date: Dec. 7, 2016

(87) PCT Pub. No.: WO2015/189829
PCT Pub. Date: Dec. 17, 2015

(65) Prior Publication Data
US 2017/0124391 A1 May 4, 2017

(30) Foreign Application Priority Data

Jun. 12, 2014 (IT) .............................. MI2014A1074

(51) Int. Cl.
*G06K 9/00* (2006.01)
*A61B 3/113* (2006.01)
(Continued)

(52) U.S. Cl.
CPC ........ *G06K 9/00604* (2013.01); *A61B 3/0025* (2013.01); *A61B 3/0041* (2013.01);
(Continued)

(58) Field of Classification Search
None
See application file for complete search history.

(56) References Cited

U.S. PATENT DOCUMENTS

| 2003/0123027 A1* | 7/2003 | Amir ...................... A61B 3/113 |
| | | 351/209 |
| 2014/0320397 A1* | 10/2014 | Hennessey ............. A61B 3/113 |
| | | 345/156 |

FOREIGN PATENT DOCUMENTS

| EP | 2685351 A1 | 1/2014 |
| JP | 2012065781 A | 4/2015 |
| WO | 2013059940 A1 | 5/2013 |

OTHER PUBLICATIONS

International Search Report & Written Opinion for PCT/IB2015/054478 dated Oct. 5, 2015.

\* cited by examiner

*Primary Examiner* — Amare Mengistu
*Assistant Examiner* — Shawna T Stepp Jones
(74) *Attorney, Agent, or Firm* — Dorsey & Whitney LLP

(57) ABSTRACT

A calibration method for an eye tracker provides for the defining of at least one first region of attraction of a first image to be displayed to a user; acquiring a first sequence of data relative to the eye movement of a user who is looking at the first image by means of an eye tracker; calculating at least a plurality of first calibration positions by means of respective calibration functions on the basis of a first gaze determined from the first sequence of data relative to eye movement; assigning a first score to each calibration function on the basis of the respective first calibration position and the first region of attraction; and selecting one of the calibration functions on the basis of the score.

17 Claims, 3 Drawing Sheets

(51) Int. Cl.
*G06F 3/01* (2006.01)
*G06F 3/0484* (2013.01)
*G06T 7/80* (2017.01)
*G06T 7/73* (2017.01)
*A61B 3/00* (2006.01)

(52) U.S. Cl.
CPC .............. *A61B 3/113* (2013.01); *G06F 3/013* (2013.01); *G06F 3/04842* (2013.01); *G06T 7/74* (2017.01); *G06T 7/80* (2017.01); *G06T 2207/30201* (2013.01)

DEVICE AND METHOD OF CALIBRATION FOR AN EYE TRACKER AND EYE CONTROL EQUIPMENT COMPRISING SAID CALIBRATION DEVICE

TECHNICAL FIELD

The present invention relates to a device and method of calibration for an eye tracker, and to eye control equipment comprising said calibration device.

BACKGROUND ART

The devices for tracking eye movement (commonly referred to as "eye trackers") normally require performing a calibration step. During the calibration process, in fact, some specific eye parameters of the user are deducted to correlate a given pupil position at a certain observed point.

Usually, during the calibration step the user is prompted to at least stare at three predefined points of a screen for a few seconds. The calibration is performed by assuming that the user will actually stare at said points, when required, and that the pupil will not suffer expansion due to a change in lighting conditions.

The calibration procedure described above requires, therefore, attention and cooperation from the user.

Moreover, in most cases the calibration procedure is performed periodically to compensate for any environmental change or to adapt to possible eye fatigue of the user.

The calibration procedure may therefore be annoying and stressful as it requires time and collaboration on behalf of the user.

Moreover, a calibration procedure of this kind is unacceptable for applications open to different users such as interactive interfaces of game or content selection, attention control applications while driving, etc.

The need is felt to minimize the effort required by the user by making the calibration substantially imperceptible.

The document US 2011/0310006, for example, describes a solution wherein the calibration is "masked" through the eye monitoring while the user performs specific actions. It is assumed that the eye is pointing to a set point while these actions take place (e.g. while pressing a button it is assumed that the eye is turned to the button). However, this method still requires collaboration by the user and not always is effective, especially since it often happens that the user performs the action without actually staring at the intended point.

DISCLOSURE OF INVENTION

It is therefore an object of this invention to provide a method which is free from the drawbacks of the prior art highlighted here; in particular, it is an object of the invention to provide a calibration method that is imperceptible by the user and that, at the same time, guarantees a precise and reliable calibration.

According to these purposes, the present invention relates to a calibration method as claimed in claim 1.

In this way, the calibration is performed without requiring any cooperation by the user. Calibration is in fact performed without the user noticing it. Moreover the calibration is optimized by means of the calibration function selection which is evaluated as the best among a plurality of calibration functions.

It is a further object to provide a calibration device which is able to perform an accurate and reliable calibration and, at the same time, is imperceptible to the user.

According to these objects, the present invention relates to a calibration device as claimed in claim 9.

BRIEF DESCRIPTION OF THE DRAWINGS

Further characteristics and advantages of the present invention will become clear from the following description of a non-limiting embodiment, with reference to the figures of the accompanying drawings, wherein.

BEST MODE FOR CARRYING OUT THE INVENTION

Figure 1:
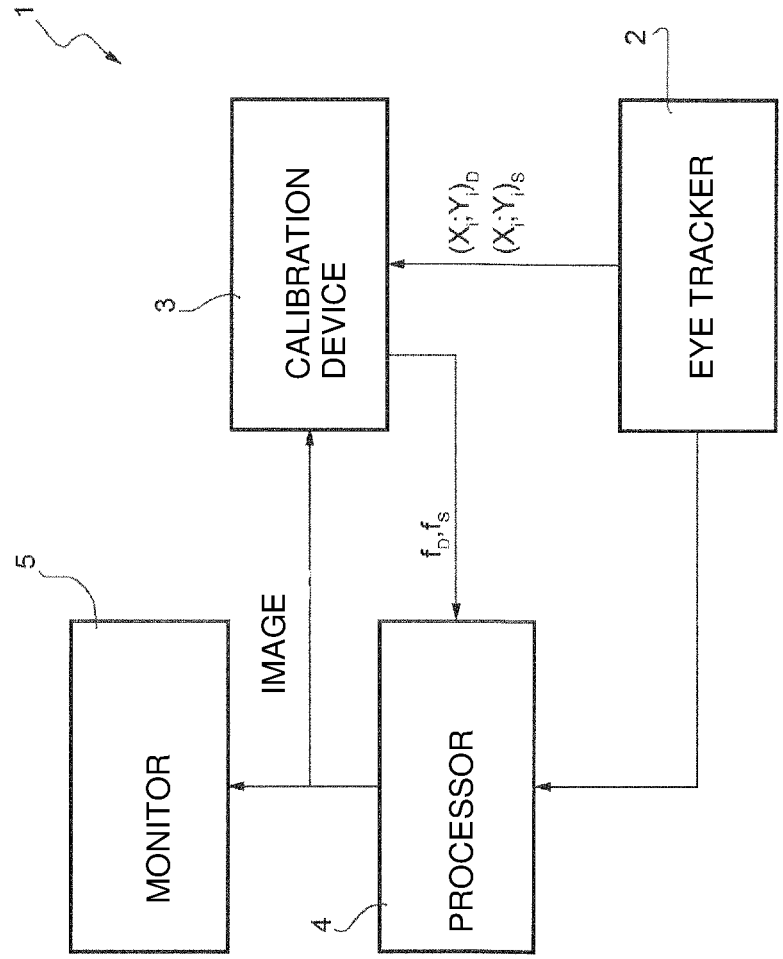
FIG. 1 is a block schematic representation of the eye control equipment according to the present invention.

In FIG. 1 an eye control equipment according to the present invention is indicated with the reference number 1.

In the non-limiting example described and illustrated here the eye control equipment 1 is for selecting the contents of a software run by a processor and displayed on a monitor.

It is understood that for eye control equipment is meant any equipment that receives input data relative to the eye movement of one or more users. For example, the eye control equipment may be configured for monitoring the attention of a user while driving, or to operate and adjust the movement of a device, to move the user's attention on the basis of its path of visual exploration, or to monitor the eyes of non-collaborative subjects such as infants.

The eye control equipment 1 comprises an eye tracker 2, a calibration device 3, a processor 4 and a monitor 5.

The device for tracking eye movement 2, here and hereinafter identified with the term "eye-tracker", is configured for recording the position and orientation of the eye of the monitored user. Preferably, the eye tracker 2 comprises at least one camera (not shown in the attached images) focused on the plane of the iris diaphragm of the user and an image processing system for processing images thus acquired (not visible in the attached figures).

The image processing system provides a sequence of coordinates corresponding to the current eye position. In particular, the image processing system provides a pair of coordinates for each eye position, preferably Cartesian coordinates.

Preferably, the eye tracker 2 is configured for providing a sequence of actual coordinates for the right eye $(x_1; y_1)_D$, $(x_2; y_2)_D$, ... $(x_n; y_n)_D$ (hereinafter referred briefly with $(x_i; y_i)_D$) and a sequence of actual coordinates for the left eye $(x_1; y_1)_S$, $(x_2; y_2)_S$, ... $(x_n; y_n)_S$ (hereinafter referred to briefly with $(x_i; y_i)_S$).

The sequence of coordinates for the right eye $(x_i; y_i)_D$ defines the scanpath made by the right eye of the user, while the sequence of coordinates for the left eye $(x_i; y_i)_S$ defines the scanpath made by the left eye of the user.

The calibration device 3 is configured for determining at least one optimal calibration function to be fed to the processor 4, which, as we shall see in more detail below, corrects the sequence of coordinates corresponding to the current eye position on the basis of the optimal calibration function recorded and controls the content selection software.

In the non-limiting example herein described and illustrated, the calibration device 3 is configured for determining at least one optimal calibration function for the right eye fD and an optimal calibration function for the left eye fS to be fed to the processor 4.

Figure 2:
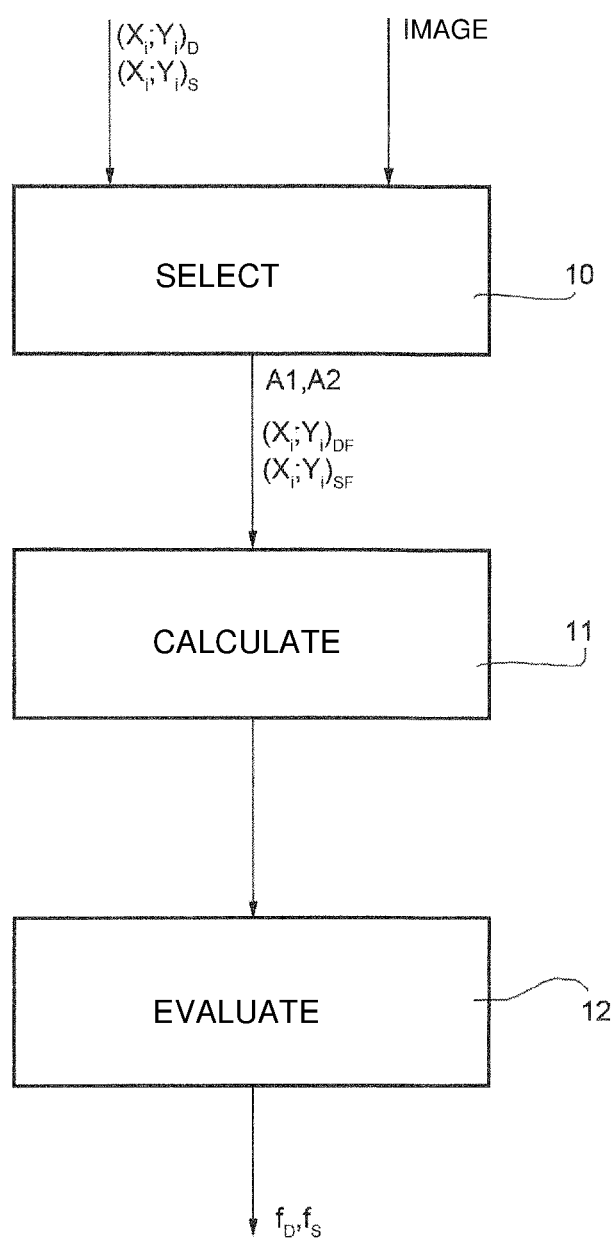
FIG. 2 is a block schematic representation of the calibration device according to the present invention.

With reference to FIG. 2, the calibration device 3 comprises a selection module 10, a calculation module 11, an evaluation module 12.

The selection module 10 is configured for determining coordinates relative to user eye gazes and to define at least one first attraction region A1 of the current image displayed on the monitor 5 and brought to the attention of the user.

Normally, in fact, the eye of the user stops observing some targets for a certain period of time. For gaze, meaning therefore, a point observed for a given period of time. However, the gaze of the user is never at rest on a precise point even when stopping to observe a target, but rather moves around the target observed. The coordinates of each gaze are then formed starting from the coordinates of the observation scores in a given area with a high observation density and during a given time slot.

Preferably, the calibration device 3 is configured for determining the coordinates of each gaze by means of a simple average between the coordinates of the observation scores selected in a specific observation area during a given lapse of time.

Alternatives provide for determining the coordinates of each gaze by calculating the center of gravity or the calculation of a weighted average or other types of calculation.

In the non-limiting example described and illustrated here, the selection module 10 is configured for determining a sequence of coordinates relative to right eye gazes $(x_i; y_i)_{DF}$ and a sequence of coordinates relative to left eye gazes $(x_i; y_i)_{SF}$.

The selection module 10 is also configured for recording and determine additional indicators for the monitored movements of the eye of the user. For example, the selection module 10 herein described and illustrated is suited to determine the duration of each gaze, the spatial density of gazes, the number of gazes by area of interest, the sum of the duration of gazes in a specific area ("gaze"), the time elapsed until the first gaze and parameters relative to saccadic movements.

As already mentioned, the selection module 10 is configured for defining at least one first region of attraction A1 of the current image displayed on the monitor 5 and brought to the attention of the user. In the non-limiting example herein described and illustrated the identification of the regions of attraction for each current image displayed by the monitor is previously performed and stored in the selection module 10. Preferably the previous identification is based on experimental tests.

In detail, the selection module 10 is configured for identifying a first region of attraction A1 and a second region of attraction A2 of the current image displayed on the monitor 5.

An alternative provides that the definition of the regions of attraction is performed in real time starting from the current image displayed by means of statistical calculation that identify the regions that would most likely attract the attention of the user.

Figure 3:
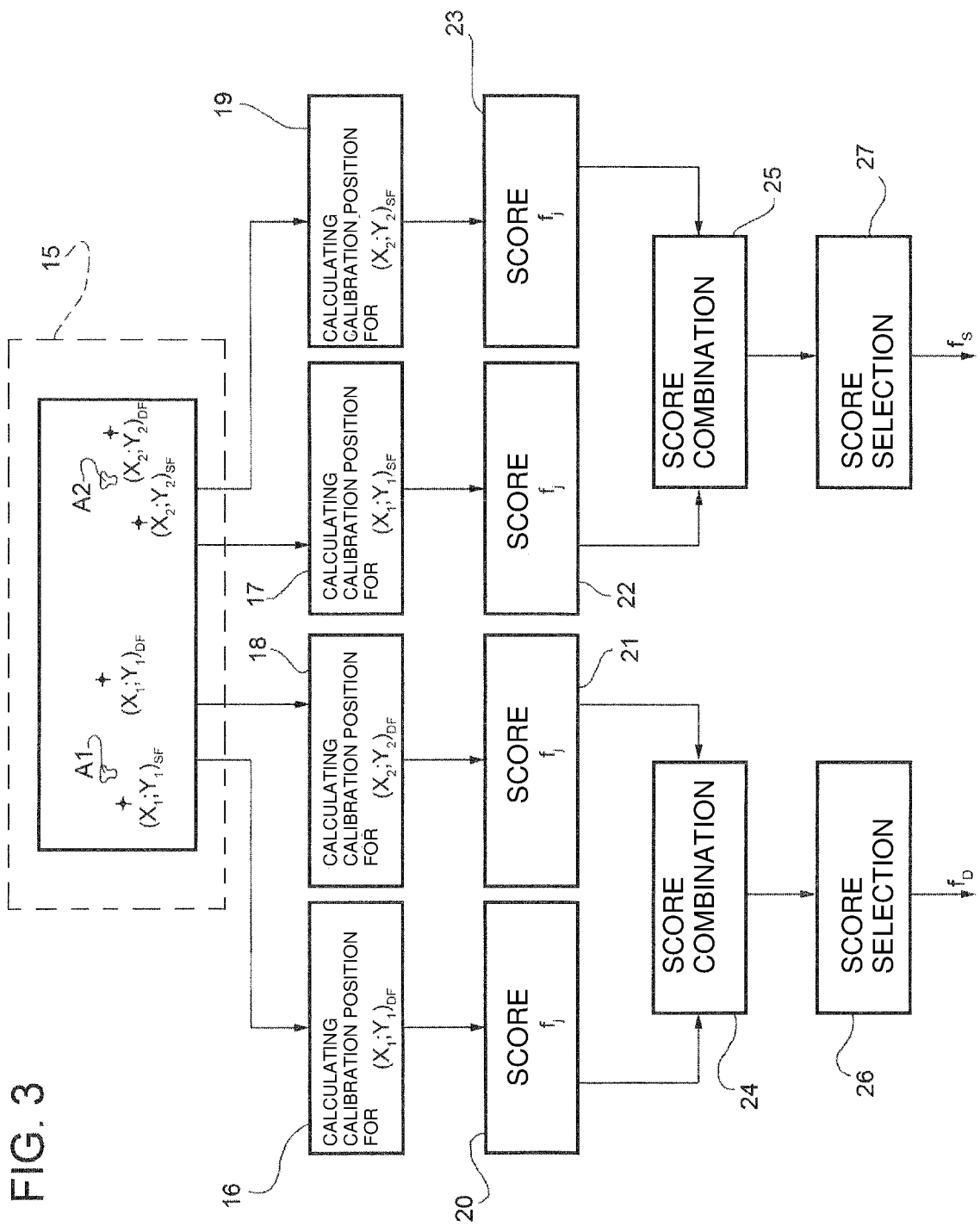
FIG. 3 is a flow diagram relating to some steps of the calibration method according to the present invention.

In FIG. 3 a block 15 which summarizes the activity carried out by the selection module 10 is illustrated.

With reference to FIG. 2, the sequence of coordinates relative to the gazes of the right eye $(x_i; y_i)_{DF}$ and the sequence of coordinates relative to the gazes of the left eye $(x_i; y_i)_{SF}$ identified by the selection module 10 are sent to the calculation module 11.

The calculation module 11 is configured for calculating a plurality of calibration positions for the gazes of the right eye $(x_i; y_i)_{DF}$ (block 16 of FIG. 3) and/or of the gazes of the left eye $(x_i; y_i)_{SF}$ (block 17 of FIG. 3) by means of respective calibration functions $f_1, f_2 \ldots f_n$ (hereinafter referred to briefly with $f_j$).

Therefore, for each gaze of the right eye $(x_i; y_i)_{DF}$ the following calculations are made:

$$P_{jD}=(x; y)_{jD}=f_j((x_i; y_i)_{DF})$$

For each gaze of the left eye $(x_i; y_i)_{SF}$ the following calculations are made:

$$P_{jS}=(x; y)_{jS}=f_j((x_i; y_i)_{DF})$$

In the not-limiting example described and illustrated, the coordinates of the plurality of calibration positions for the gazes of the right eye $P_{jD}$ and for the gazes of the left eye $P_{jS}$ are calculated individually in this way:

$$P_{jD}=(x; y)_{jD}=(f_j(x_i); f_j(y_i))_{DF}$$

$$P_{jS}=(x; y)_{jS}=(f_j(x_i); f_j(y_i))_{SF}$$

In the non-limiting example herein described and illustrated the calibration functions $f_j$ are approximately 1000. The number of calibration functions $f_j$ used essentially depends on the accuracy desired, on the type of application of the eye control equipment 1 (for example in eye control equipment 1 for an interactive game a calibration accuracy less than that required by eye control equipment for voice communication is required), and of the computing power of the calibration device 3 itself.

Preferably the calibration functions $f_j$ are first degree functions. An alternative provides that the calibration functions $f_j$ comprise functions having degree greater than the first. In the non-limiting example herein described and illustrated, the functions $f_j$ are functions obtained by experimental tests and stored in the calculation module 11.

The plurality of calibration positions $P_{jD}, P_{jS}$ are sent to the evaluation module 12, which is configured for determining, among the plurality of calibration functions $f_j$ adopted, a calibration function optimal for the right eye $f_D$ and a calibration function optimal for the left eye $f_S$ to be fed to the processor 4.

In the non-limiting example herein described and illustrated, the evaluation module 12 is configured for:
  assigning a score to each calibration function $f_j$ on the basis of the respective calibration positions $P_{jD}, P_{jS}$ of the plurality of calibration positions for the right eye gazes (block 20 in FIG. 3) and for the left eye gazes (block 22 of FIG. 3) with respect to the region of attraction A1 of the current image;
  storing the score assigned to the region of attraction A1;
  assigning a score to each calibration function $f_j$ on the basis of the respective calibration positions $P_{jD}, P_{jS}$ of the plurality of calibration positions for the right eye gazes (block 21 in FIG. 3) and for the left eye gazes (block 23 of FIG. 3) with respect to the region of attraction A2 of the current image;
  storing the score assigned to the region of attraction A2;
  combining the scores given to each calibration function for the right eye (block 24 of FIG. 3) and combining the scores given to each calibration function for the left eye $f_j$ (block 25 of FIG. 3);

selecting a calibration function optimal for the right eye $f_D$ having maximum final score (block 26 of FIG. 3) and a calibration function optimal for the left eye $f_S$ having maximum final score (block 27 of FIG. 3).

In the non-limiting example herein described and illustrated the assignment of the score is performed on the basis of the distance between the calibration point $P_{jD} P_{jS}$ relative to a specific calibration function $f_j$ and the respective region of attraction A1, A2. The further the calibration point $P_{jD} P_{jS}$ is from the respective region of attraction A1, A2 the lower is the score.

The combination of the scores is preferably performed by means of a weighted sum of the scores. The weight assigned to each score depends on the attraction capacity of the respective region of attraction. The weights assigned to each region of attraction are previously determined.

The calibration device 3 is continuously active and the scores assigned to each calibration function $f_j$ are stored so that successive calibrations take account of the scores awarded by the previous calibrations.

For example, if a further score is assigned to each calibration function $f_j$ with respect to a further region of attraction different than the region of attraction A1 and A2, said further score would be added to the scores previously assigned with respect to the regions of attraction A1 and A2. Therefore, if a second image is brought to the user's attention, the calibration device 3 would proceed again to assign scores to each new calibration function $f_j$ with respect to a region of attraction of the second image and add these new scores to the scores previously assigned. In this way, the calibration function optimal for the right eye $f_D$ and for the left eye $f_S$ is continuously calculated in an iterative way. This allows the calibration device 3 to adapt to any change of user, environmental conditions, etc.

An alternative not illustrated provides that the selection module identifies a single region of attraction and a plurality of gazes and that the evaluation module 12, for each gaze, assigns to the calibration functions $f_j$ only the score calculated with respect only to the region of attraction recorded.

The calibration functions optimal for the right eye $f_D$ and for the left eye $f_S$ which are continuously calculated by the calibration device 3 are fed to the processor 4. The processor 4 corrects the right eye $(x_i; y_i)_D$ and the left eye $(x_i; y_i)_S$ sequence coordinates recorded by the eye-tracker 2 by using the calibration functions $f_D$ e $f_S$. Once the correct values of the sequences of the right eye $(x_i; y_i)_D$ and the left eye $(x_i; y_i)_S$ coordinates are obtained, the processor 4 calculates, preferably, an average between the correct coordinates of the right eye and the respective correct coordinates of the left eye. The average will be used as a command for the selection of the software contents.

The processor 4 is, furthermore, configured for recording any anomalies between right eye and left eye, e.g. determined by strabismus. In this case, the processor 4 does not calculate the average of the right eye correct coordinates and the left eye correct coordinates, but only counts the correct coordinates of the dominant eye as a command for selecting the software contents.

In the non-limiting example herein described and illustrated the calibration device 3 is separated from the processor 4. An alternative not illustrated provides that the calibration device 3 is integrated with the processor 4 or that the processor 4 is integrated with the calibration device 3.

A further alternative provides that the calibration device 3 and the processor 4 are integrated with the eye tracker 2.

Advantageously, the calibration device 3 can be used to perform the calibration for any type of eye tracker 2.

Moreover the calibration device 3 is suited for performing a continued calibration not influenced by environmental changes, by the sudden change of user or by any eye fatigue. In this way the eye control equipment can be used by multiple users in sequence. The calibration, in fact, is continuously adapted to the user's current conditions. Said aspect is particularly advantageous for game interfaces and content selection. Thanks to the calibration device according to the present invention, in fact, the user is not required to be collaborative.

The calibration device 3 according to the present invention, in fact, is able to adapt to any condition thanks to the fact that the optimal calibration function is continuously calculated and evaluated.

As the scores assigned to the calibration functions accumulate, the ranking is updated and shows the best calibration function. Said calibration method results to be robust and able to adapt to any situation. The calibration method according to the present invention, moreover, is very fast, as the optimal calibration function emerges almost immediately, and is completely autonomous, as it did not require any validation of the recorded optimal calibration function.

Finally, it is evident that the eye control equipment, the method and the calibration device described may be modified and varied without departing from the scope of the appended claims.

The invention claimed is:

1. Calibration method for an eye tracker comprising:
defining at least a first region of attraction of a first image to he displayed to a user;
acquiring a first sequence of data relative to eye movement of the user who is looking at the first image using the eye tracker;
determining a first gaze from the first sequence of data relative to the eye movement;
calculating at least a plurality of first calibration positions using respective calibration functions on the basis of the first gaze;
assigning a first score to each calibration function on the basis of the respective first calibration position and the first region of attraction, the first score being calculated on the basis of the distance between the first calibration position and the respective first region of attraction;
selecting one of the calibration functions on the basis of the first score;
determining a second gaze from the first sequence of data relative to the eye movement:
calculating at least a plurality of second calibration positions, each using one of the respective calibration functions on the basis of the second gaze;
assigning a second score to each calibration function on the basis of the distance between the second calibration position and the first region of attraction;
combining the second score with the first score of each calibration function to obtain a final score by calculating a weighted sum of the first score and the second score, wherein the weight assigned to each score depends on the attraction capacity of the first region of attraction; and
selecting the calibration function having a maximum final score.

2. A method according to claim 1, comprising:
defining at least one second region of attraction of the first image;
determining a third gaze from the first sequence of data relative to the eye movement;

calculating at least a plurality of third calibration positions, each using one of the respective calibration functions on the basis of the third gaze;
assigning a third score to each calibration function on the basis of the respective third calibration position and the second region of attraction;
combining the third score with at least the first score of each calibration function to obtain a final score; and
selecting one of the calibration functions on the basis of the final score.

3. A method according to claim 1, comprising:
defining at least a third region of attraction of a second image, different from the first image, to be displayed to the user;
acquiring second data relative to the eye movement recorded by the eye tracker of the user who is looking at the second image;
determining a fourth gaze from the second sequence of data relative to the eye movement
calculating at least one plurality of fourth calibration positions each using one of the respective calibration functions on the basis of the fourth;
assigning a fourth score to each calibration function on the basis of the respective fourth calibration position and the third region of attraction;
combining the fourth score with at least the first score of each calibration function to obtain a final score; and
selecting one of the calibration functions on the basis of the final score.

4. A method according to claim 1, comprising storing the first score and the second score and, if present, the third score and/or the fourth score assigned to each respective calibration function.

5. A method according to claim 1, wherein the defining at least one region of attraction of an image comprises calculating the position and extension of the region of attraction on the basis of the image using statistical calculation instruments.

6. A method according to claim 1, wherein assigning a first score and a second score and, if present, a third score and/or a fourth score to each respective calibration function on the basis of the respective calibration position comprises assigning a score according to the distance between the calibration position and the respective region of attraction.

7. A method according to claim 1, wherein combining the second score and, if present, the third score and/or the fourth score with the first score of each calibration function to obtain a final score comprises calculating a weighted sum of the first score, second score and, if present, the third score and/or the fourth score; the weight of the first score, second score and, if present, the third score and/or the fourth score is determined on the basis of the attraction capacity of the respective region of attraction.

8. A method for operating eye control equipment comprising:
performing a procedure that includes the display of images using a monitor and the acquisition of data relative to the eye movement of a user using an eye tracker;
simultaneously performing a calibration method as claimed in claim 1 using the images displayed and the data acquired during the procedure.

9. A non-transitory computer readable medium comprising instructions that can be read and run by a computer and configured to cause the computer to implement the method claimed in claim 1.

10. A calibration device for an eye tracker comprising:
a selection module configured to define at least one first region of attraction of a first image to be displayed to a user and to determine a first gaze and a second gaze from a first sequence of data relative to the eye movement of the user who is looking at the first image, recorded using the eye tracker;
a calculation module configured to calculate a plurality of first calibration positions using respective calibration functions on the basis of the first gaze, wherein the calculation module is further configured to calculate at least a plurality of second calibration positions, each using one of the respective calibration functions on the basis of the second gaze determined from the first sequence of data;
an evaluation module configured to assign a first score to each calibration function on the basis of the distance between the first calibration position and the respective first region of attraction and to select one of the calibration functions on the basis of the first score; wherein the evaluation module is configured to assign a second score to each calibration function on the basis of the distance between the second calibration position and the first region of attraction, to combine the second score of each calibration function with the first score so as to obtain a final score via a weighted sum of the first score and the second score, wherein the weight assigned to each score depends on the attraction capacity of the region of attraction, and to select the calibration function having a maximum final score.

11. A device according to claim 10, wherein:
the selection module is configured to define at least one second region of attraction of the first image and to determine a third gaze from the first sequence of data;
the calculation module is configured to calculate at least one plurality of third calibration positions, each using one of the respective calibration functions on the basis of the third gaze;
the evaluation module is configured to assign a third score to each calibration function on the basis of the respective third calibration position and the second region of attraction, combine the third score of each calibration function with at least the first score so as to obtain a final score, and select one of the calibration functions on the basis of the final score.

12. A device according to claim 10, wherein:
the selection module is configured to define at least one third region of attraction of a second image, different from the first image, to be displayed to a user, wherein the selection module is further configured determine a fourth gaze from a second sequence of data relative to the eye movement of the user who is looking at the second image, recorded using the eye tracker;
the calculation module is configured to calculate at least a plurality of fourth calibration positions, each using one of the respective calibration functions on the basis of the fourth gaze;
the evaluation module is configured to assign a fourth score to each calibration function on the basis of the respective fourth calibration position and the third region of attraction, combine the fourth score of each calibration function with at least the first score so as to obtain a final score, and select one of the calibration functions on the basis of the final score.

13. A device according to claim 10, wherein the evaluation module is configured to store the first score and the second score and, if present, the third score and/or the fourth score assigned to each respective calibration function.

14. A device according to claim 10, wherein the selection module is configured to define at least one region of attraction of an image using calculation of the position and extension of the region of attraction on the basis of the image using statistical calculation instruments.

15. A device according to claim 10, wherein the evaluation module is configured to assign a first score and a second score and if present, a third score and/or a fourth score to each respective calibration function according to the distance between the calibration position and the respective region of attraction.

16. A device according to claim 10, wherein the evaluation module is configured to combine the second score and, if present, the third score and/or the fourth score with the first score of each calibration function to obtain a final score via a weighted sum of the first score and a second score and if present, a third score and/or a fourth score; the weight of each score being determined on the basis of the attraction capacity of the respective region of attraction.

17. Eye control equipment comprising:
a monitor configured to display at least one first image;
an eye tracker configured to record a first sequence of data relative to the eye movement of a user who is looking at the first image;
a calibration device of the type claimed in claim 10.

* * * * *